(12) United States Patent
Heinz et al.

(10) Patent No.: US 8,299,282 B2
(45) Date of Patent: Oct. 30, 2012

(54) CONTINUOUS METHOD FOR THE HETEROGENICALLY CATALYZED ESTERIFICATION OF FATTY ACIDS

(75) Inventors: Dieter Heinz, Shanghai (CN); Leslaw Mleczko, Dormagen (DE); Shaibal Roy, Köln (DE); Heinrich Morhenn, Köln (DE); Wulf Dietrich, Köln (DE)

(73) Assignee: Bayer Technology Services GmbH, Leverkusen (DE)

( * ) Notice: Subject to any disclaimer, the term of this patent is extended or adjusted under 35 U.S.C. 154(b) by 248 days.

(21) Appl. No.: 12/738,115

(22) PCT Filed: Oct. 16, 2008

(86) PCT No.: PCT/EP2008/008763
§ 371 (c)(1),
(2), (4) Date: Apr. 15, 2010

(87) PCT Pub. No.: WO2009/056231
PCT Pub. Date: May 7, 2009

(65) Prior Publication Data
US 2010/0249442 A1 Sep. 30, 2010

(30) Foreign Application Priority Data
Oct. 30, 2007 (DE) .................. 10 2007 052 065

(51) Int. Cl.
*C11C 1/02* (2006.01)
*B01D 3/00* (2006.01)

(52) U.S. Cl. .......... 554/174; 554/175; 554/17; 554/124; 203/45; 203/6

(58) Field of Classification Search .................. None
See application file for complete search history.

(56) References Cited

U.S. PATENT DOCUMENTS
4,698,186 A 10/1987 Jeromin et al.
2005/0113589 A1* 5/2005 Katayama et al. ............ 554/174

FOREIGN PATENT DOCUMENTS
| DE | 1 960 0025 A1 | 7/1997 |
| EP | 0 192 035 A2 | 8/1986 |
| GB | 384715 | * 5/1932 |
| GB | 2145079 A | * 3/1985 |
| WO | 2007/083213 A | 7/2007 |
| WO | 2007/093326 A | 8/2007 |

OTHER PUBLICATIONS

Henkel KGGA, Preparation of fatty acids with low acid values, useful as precursors for esterification, 1997, English translation of DE19600025, 11 pages.*

Athanassiadis, A., et al., The deacidification of Vegetable oils by distillation during deodorization, 1988, Fat. Sci. Technol., vol. 90, No. 13, pp. 522-526.*

(Continued)

*Primary Examiner* — Yate K Cutliff
(74) *Attorney, Agent, or Firm* — Norris McLaughlin & Marcus PA

(57) ABSTRACT

Continuous method for the esterification of free fatty acids in plant and animal fats with alcohols using a heterogenic acid catalyst.

17 Claims, 1 Drawing Sheet

OTHER PUBLICATIONS

Martinello, M., et al., Grape seed oil deacidification by molecular distillation: Analysis of operative variables influence using the response surfact methodology, 2006, Journal of Food Engineering, vol. 81. pp. 60-64.*

Mittelbach, Remschmidt, Biodiesel—The comprehensive handbook 3rd ed., 2006, p. 60.

DIN EN ISO 2114 Plastics (polyester resins) and paints and varnishes (binders)—Determination of partial acid value and total acid value (ISO 2114:2000).

* cited by examiner

CONTINUOUS METHOD FOR THE HETEROGENICALLY CATALYZED ESTERIFICATION OF FATTY ACIDS

This is a 371 of PCT/EP2008/008763 filed 16 Oct. 2008 (international filing date), which claims foreign priority benefit under 35 U.S.C. §119 of German Patent Application No. 10 2007 052 065.6 filed Oct. 30, 2007.

The invention relates to a continuous process for esterifying free fatty acids in vegetable and animal fats with alcohols using a heterogeneous acidic catalyst.

BACKGROUND OF THE INVENTION

Vegetable and animal fats and oils often contain considerable proportions of free fatty acids. According to the source of the fatty raw material, the content of free fatty acids may be between 0 and 100% by weight. In production processes for biodiesel by transesterifying triglycerides, this proportion of free fatty acids cannot be reacted with methanol to give the corresponding fatty acid methyl esters and leads to yield losses, or to the effect that raw materials with a high content of free fatty acids are unsuitable for biodiesel production.

A pretreatment of the fats is therefore frequently necessary, in which the content of free fatty acids is reduced and the free fatty acids are converted by esterification with alcohol to the fatty acid alkyl ester target product.

The literature discloses deacidification processes for fats and oils, for example by removal of free fatty acids with the aid of a steam distillation (Ullmann's Encyclopedia of Industrial Chemistry, Electronic Edition, Topic "Fats and Fatty Oils", p. 30). Such a removal allows the acid number of the fats to be reduced to values below 0.2, such that the resulting fats or oils can be converted in a transesterification process.

In this connection, the acid number specifies the mass of potassium hydroxide in mg which is required to neutralize 1 g of the sample to be analysed (DIN 53402, newest version DIN EN ISO 2114).

The literature discloses the esterification of free fatty acids with methanol with the aid of a homogeneous acidic catalyst, e.g. p-toluenesulphonic acid or $H_2SO_4$ (Mittelbach, Remschmidt, Biodiesel—The comprehensive handbook 3rd ed., 2006, p. 60). However, this process requires a relatively difficult catalyst removal by neutralization and washing with alcohol or water, which does not allow the catalyst used to be recovered and gives rise to considerable amounts of wastewater.

EP 0192035 and DE 196 00 025 describe a process for deacidifying fats or oils, in which acidic solid ion exchange resins are used as catalysts, and whose removal from the reaction mixture is followed by removal of the water by-product. In this case, the esterification of the free fatty acids is carried out without preceding removal of the free fatty acids in the overall mixture of fatty acid and oil. Since the free fatty acids in most cases make up a comparatively low proportion of the overall amount of fat and oil (usually 2-20 percent by weight, in rare cases even more than 30% by weight), this process leads to an unfavourable space-time yield both in the esterification and in a subsequent transesterification, but more particularly with regard to the esterification of the free fatty acids, since an additional mass flow of inert components is also processed in the reaction.

DE 196 00 025 discloses, inter alia, that it may be advantageous to add additional free fatty acids to the pre-esterification. Under some circumstances, this can serve to reduce the relative proportion by mass of inert material in the starting material of the process. However, no fundamental solution to the technical problem of achieving higher conversions and consequent increased space-time yields of a pre-esterification is disclosed, since, more particularly, the free fatty acids used for the increase in the proportion of the free fatty acids preferably stem from a later process step and are therefore subjected to further processing steps. This is especially true because soap cleavage by means of metered addition of homogeneously dissolved acids becomes necessary here. The maximum space-time yield disclosed in DE 196 00 025 is 34 g of fatty acid methyl ester per litre of reactor volume and hour.

For economically viable processing of fatty raw materials to biodiesel where the fatty raw materials contain a proportion of free fatty acids, it is therefore an object of the invention to develop a process which achieves esterification of the free fatty acids with high space-time yield and simultaneously enables recovery of the esterification catalyst.

SUMMARY

It has been found that, surprisingly, this object is achieved by a continuous process for esterifying free fatty acids present in starting materials, which is characterized by at least the steps of
1) removing the free fatty acids from the remaining starting material by means of a customary deacidification process,
2) optionally reacting the deacidified starting material remaining after step 1) in the form of a transesterification to obtain fatty acid alkyl esters,
3) reacting the free fatty acids with alcohols using at least one acidic catalyst in a fixed bed, in the form of an esterification reaction,
4) optionally removing the water formed as a by-product in step 3), optionally together with at least a portion of the alcohol unconverted in step 3),
5) optionally further converting the dewatered product obtained from step 4), optionally with addition of further alcohol, using at least one acidic catalyst in a fixed bed, in the form of an esterification reaction,
6) mixing the reaction product obtained from step 3) and/or the reaction product which may be obtained from step 5) with the remaining starting material obtained from step 1) and/or the fatty acid alkyl esters obtained from step 2).

In connection with the present invention, starting materials are all fats and/or oils which include at least a proportion of free fatty acids, and a proportion of fatty acid glycerides. Preference is given to starting materials which possess a proportion of free fatty acids greater than 2% by weight.

DETAILED DESCRIPTION

Possible sources of the starting materials are oils and/or fats of vegetable or animal origin. Nonexclusive examples of starting materials of vegetable origin are rapeseed oil, palm oil, jatropha oil, coconut fat, etc. Nonexclusive examples of starting materials of animal origin are bovine tallow, fish oil, pork lard, etc.

In the context of the present invention, fatty acids are all aliphatic carboxylic acids of the formula (I)

$$R^1\text{—CO—OH} \qquad (I),$$

or mixtures of different compounds corresponding to formula (I), which are already present in the starting materials as fatty acids, referred to hereinafter as free fatty acids, or can be obtained by hydrolytic cleavage (saponification) of the fatty acid glycerides present in the starting materials. Fatty acid alkyl esters therefore describe the alkyl esters of fatty acids which are obtained after esterification and/or transesterification or are already present in the starting material.

In this context, $R^1$ in formula (I) preferably includes aliphatic carbon chains having 6 to 22 carbon atoms and optionally one or more double bonds.

Fatty acid glycerides are mono-, di- or triglycerides of the fatty acids described above.

In connection with the present invention, alcohols refer to mono- or polyhydric $C_1$ to $C_5$ alcohols or mixtures thereof Preference is given to monohydric $C_1$ to $C_3$ alcohols. Very particular preference is given to methanol. In this context, the hydricity of an alcohol describes the number of covalently bonded hydroxyl groups present in the inventive alcohol.

Step 1) of the process according to the invention is effected preferably by a customary process known to those skilled in the art by the terms of distillation, rectification or extraction.

Step 1) of the process according to the invention is particularly advantageous because the preceding removal of the free fatty acids from the remaining starting material allows the sizes of reactor construction for the esterification to be selected at a significantly lower level owing to the smaller mass flows to be processed, and the esterification to be performed in a monophasic system. Both facts lead to a considerably reduced risk of miscalculation in the scaleup of reactors in which the process according to the invention can be carried out.

A further advantage of step 1) of the process according to the invention can be achieved in the solution of the problem of reducing catalyst inactivation of the heterogeneous catalyst in the conversion, for example, in step 3) and/or step 5) of the process according to the invention. The removal of the free fatty acids from the remaining starting material also removes large portions of any catalyst poisons from the free fatty acids, such that they can no longer lower the activity of the acidic catalyst.

In connection with the present invention, catalyst poisons include, for example, the ions of alkali metals and alkaline earth metals. Nonexclusive examples mentioned here include the ions of sodium, potassium, calcium, strontium, etc.

When a reaction in the form of a transesterification in step 2) of the deacidified starting material remaining after step 1) is intended, the deacidified, remaining starting material preferably comprises fatty acid glycerides, or mixtures thereof Likewise preferably, step 2) is performed by a customary process known to those skilled in the art, such that minimum proportions and preferably no fatty acid glycerides are present in the reaction product, and a maximum amount and more preferably all remaining glycerides have been converted to glycerol and fatty acid alkyl esters.

Step 3) of the process according to the invention is preferably carried out using at least one acidic catalyst, which is characterized in that it comprises a strongly acidic ion exchange resin. More preferably, the at least one acidic catalyst is a polymeric, macroporous resin with free sulphonic acid groups. Most preferably, the at least one acidic catalyst is a catalyst which is sold by Rohm and Haas under the name Amberlyst® or a catalyst which is sold by Lanxess under the name Levatit®.

Likewise preferred are catalysts which possess an activity of at least 0.5 kg of free fatty acid per kg of catalyst and hour. This activity is particularly advantageous in that the process according to the invention is performable reliably with the advantageous catalyst hourly space velocities in step 3) and/or 5).

Likewise preferably, step 3) of the process according to the invention is performed such that it is characterized by a catalyst hourly space velocity of 0.5 to 10 kg of free fatty acid per kg of catalyst and hour. More preferably, the catalyst hourly space velocity is between $$1 \text{ and } 5 \frac{\text{kg}}{\text{kg} \cdot h}.$$

Most preferably, the catalyst hourly space velocity is between $$1.5 \text{ and } 4 \frac{\text{kg}}{\text{kg} \cdot h}.$$

A lower catalyst hourly space velocity is inefficient since more free fatty acid could be converted and thus the aim of a high space-time yield would not be met. A higher catalyst hourly space velocity leads to no longer sufficient conversions of the free fatty acids and hence also to lower space-time yields.

The catalyst hourly space velocity can be set via adjustment of the mass flow of the free fatty acids, or adjustment of the amount of catalyst.

In another preferred embodiment of the process according to the invention, step 3) is performed such that, based on the free fatty acids present in the starting material, alcohol is used in molar excess. More preferably, the molar excess is between 5 and 40. Most preferably, the molar excess is between 10 and 25 and especially preferably between 10 and 20.

In a further preferred embodiment of the process according to the invention, step 3) is performed at elevated temperature relative to room temperature (20° C.). More preferably, the temperature at which step 3) of the process according to the invention is performed is between 70 and 120° C. Most preferably, the temperature is between 80 and 95° C.

In a likewise preferred embodiment of step 3) of the process according to the invention, the reaction is performed under elevated pressure relative to standard pressure (1013 hPa). More preferably, the pressure of the process according to the invention in step 3) is selected such that it corresponds at least to the vapour pressure of the alcohol used under the other process conditions. The vapour pressures of the inventive alcohols under various ambient conditions are known to those skilled in the art, or are tabulated in the VDI-Wärmeatlass or similar reference works. Very particular preference is given to pressures below 5 bar.

A last preferred embodiment of step 3) of the process according to the invention is characterized in that the superficial velocity of the fluid phase in the fixed catalyst bed is between 1 and 5 mm/s and the length of the fixed catalyst bed is between 1 and 10 m. This achieves a likewise preferred residence time of the free fatty acids and alcohols of less than 30 minutes, this residence time being independent of the concentrations of the free fatty acids used in the starting material.

It has been found that, under the inventive and preferred conditions, a conversion based on the free fatty acids of more than 95% is achieved, which has the consequence of a significantly increased space-time yield of the fatty acid alkyl esters proceeding from free fatty acids in the starting material.

In the process according to the invention, a removal of the water formed as a by-product in step 3) can take place in step 4) of the process according to the invention. Preference is given to performing step 4) of the process according to the invention when step 4) is followed by a further conversion in step 5) of the process according to the invention. When a further conversion in step 5) of the process according to the invention is not intended, step 4) of the process according to the invention is preferably not performed either.

It is advantageous to couple the performance of step 4) of the process according to the invention to the performance of step 5) of the process according to the invention, since the removal of the water formed as a by-product, optionally together with at least a portion of the alcohol unconverted in step 3), without further conversion in step 5) of the process according to the invention, becomes energetically disadvantageous when no further conversion, for example in step 5) of the process according to the invention, is intended. The stream from step 4) would in any case, in the product of the process according to the invention, be combined again in step 6) of the process according to the invention with either the remaining starting material from step 1) or the remaining starting material transesterified in step 2) of the process according to the invention if no further conversion in step 5) were intended. A removal of water without subsequent further conversion is not conducive to an improvement in the sense of an esterification of the free fatty acids with high space-time yield. When, however, step 5) of the process according to the invention is performed once or more than once, a preceding performance of step 4) of the process according to the invention is advantageous in each case, because this shifts the equilibrium position to the side of the products via the removal of the water and hence it is possible to solve the problem of achieving higher space-time yields under energetically and hence economically advantageous conditions.

When step 4) of the process according to the invention is performed, it can be performed with or without removal of at least a portion of any residue of alcohol still present therein. Preference is given to a removal of a minimum portion of any residue of alcohol still present. More preferably, no alcohol is also removed. The removal is effected preferably by membrane processes or evaporation. Particular preference is given to effecting the removal by means of membranes.

For energetic and/or physical reasons (for example formation of an azeotrope), it may be necessary also to remove portions of the alcohol. The minimum removal of alcohol remaining, though, has the advantage that it is available for further reactions in any subsequent process stages. This includes especially the further conversion in step 5) of the process according to the invention, and also conceivable transesterifications of the fatty acid glycerides present in the starting materials after the process according to the invention.

When a further conversion of the dewatered reaction product obtained from step 4) in step 5) of the process according to the invention is intended, this can be done with or without further addition of alcohol. Preference is given to the addition of further alcohol. More preferably, the amount added in this case is lower than the amount added in step 3) of the process according to the invention. Most preferably, the alcohol removed after step 4) of the process according to the invention is replaced. Likewise preferably, step 5) is performed under the same preferred conditions with regard to temperature and/or pressure and/or catalyst hourly space velocity as step 3) of the process according to the invention. Further preferably, the same preferred superficial velocity and fixed catalyst bed length are selected in step 5) as in step 3). More preferably, step 5) constitutes a repetition of step 3) with further and/or replaced alcohol.

It has been found that, under these conditions, an overall conversion (based on free fatty acids) in the now two reaction stages of more than 99.5% is achieved.

When it is desired to further increase the conversion, preference is given to performing step 5) more than once. Particular preference is given to performing the sequence of step 4) and step 5) of the process according to the invention more than once.

The mixing in step 6) of the process according to the invention can be effected using the products from step 4) and/or step 5) with the remaining starting material of step 1) of the process according to the invention and/or, if appropriate, with the fatty acid alkyl ester obtained from step 2) of the process according to the invention. Preference is given to mixing the product from step 5) of the process according to the invention with the product from step 2) of the process according to the invention. This allows the desired maximum space-time yields to be achieved.

A particularly preferred embodiment of the invention comprises a continuous process which is characterized by a reaction stage according to step 3) and/or one of its preferred variants, a reaction stage according to step 5) and/or one of its preferred variants, and a removal according to step 4) and/or one of its preferred variants.

As compared with processes for esterifying free fatty acids with homogeneous catalysts corresponding to the prior art, the process according to the invention enables, as well as dispensing with the complicated catalyst removal (in the inventive reactor, the heterogeneous catalyst is fixed in a fixed bed, such that a catalyst removal is not required), an increase in the space-time yield.

It is possible by the process according to the invention to achieve space-time yields of fatty acid methyl ester of up to 380 g per litre of reactor volume and hour. For example, example 1 gives rise to a space-time yield of fatty acid methyl ester of 380 g per litre of reactor volume and hour. As compared with the prior art described in DE 19600025, this enables a dramatic reduction in the reactor size by more than one order of magnitude (in the abovementioned example, there is a size ratio of 11:1).

For biodiesel production, the process according to the invention thus enables significantly less expensive processing of fatty raw materials with a high proportion of free fatty acids as compared with the prior art processes and thus covers a larger and less expensive spectrum of fatty raw materials.

Preferred embodiments of the process according to the invention will be illustrated in detail below with reference to drawings, without restricting it thereto.

Figure 1:
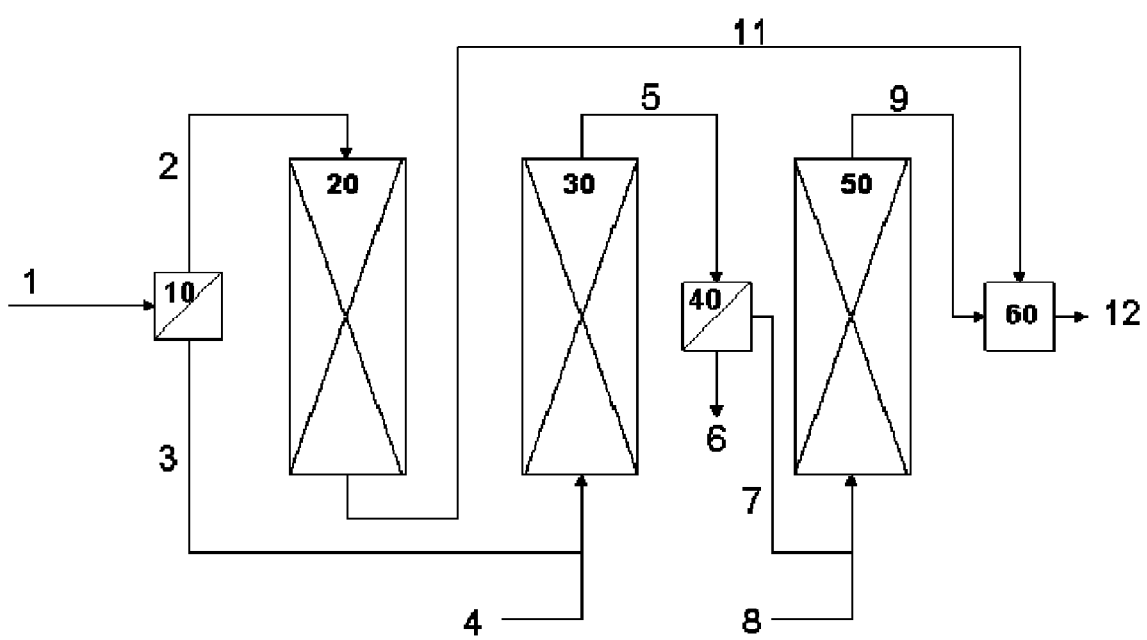
FIG. 1 shows a diagram of a particularly preferred embodiment. The starting material (1) is separated in step 1) of the process according to the invention from the free fatty acids in apparatus (10), which results in a stream comprising a residual starting material (2) and a stream comprising free fatty acids (3). The stream comprising residual starting material (2) is fed continuously to a reaction stage (20) for transesterification (though other multistage processes for transesterification are also conceivable here) in step 2) of the process according to the invention. The stream of the free fatty acids (3) is then fed to a first reaction stage (30) in step 3) of the process according to the invention, for example consisting of a flow tube reactor which contains a fixed bed consisting of a bed of catalyst particles (particle diameter 0.5 to 1 mm) with a length of 1 to 10 m, together with a stream of alcohol (4). The diameter of the fixed catalyst bed arises from the volume flow of streams (3) and (4) such that the mean residence time of these two streams in the catalyst bed is 5 to 30 min. The superficial linear flow velocity of liquid phase is 1 to 5 mm/s and the frictional pressure drop in the particle bed is less than 0.5 bar/m. The conversion of free fatty acids at the outlet of the first reaction stage (30) is then at least 95%. From the product stream (5), in a separation stage (40), in step 4) of the process according to the invention, the water by-product and the excess alcohol are evaporated and removed as stream (6). The separating stage may, for example, be a falling-film evaporator or a distillation column, which are operated at atmospheric or reduced pressure. After the separation stage, stream (7) is substantially anhydrous and is fed with further alcohol (8) to a further reaction stage (50) in step 5) of the process according to the invention. This reaction stage corresponds in terms of construction to the reaction stage (30). The conversion of free fatty acids at the outlet of the second reaction stage (corresponds to stream (9)) is at least 90% based on the stream from the first reaction stage (5) and at least 99.5% based on the stream into the first reaction stage (3). The stream (9) of the free fatty acids which have thus been converted to alkyl esters is added, in a mixer (60), in step 6) of the process according to the invention, to the stream (11) of starting material which stems from the reaction stage (20) for transesterification and has likewise been converted to alkyl esters, so as to obtain, for example, a stream of biodiesel (12).

The invention is illustrated in detail below by the examples, but without being restricted thereto.

EXAMPLES

Comparative Example 748 g/h of a mixture of rapeseed oil, oleic acid and linoleic acid with a content of free fatty acids of 10% by weight (corresponds to an acid number of approx. 20 mgKOH/g) were passed with 178 g/h of methanol at a temperature of 83° C. and a pressure of 4 bar with a residence time of 15 min over a fixed catalyst bed composed of 650 ml of acidic ion exchange resin (corresponds to 121 g of catalyst mass (dry)). The catalyst particles had a diameter of 0.8 mm and were immobilized in a fixed bed reactor with a catalyst bed length of 2.08 m. This gives rise to a catalyst hourly space velocity of 0.65 kg of free fatty acid per kg of catalyst and hour, and a superficial velocity of 2.3 mm/s In the reaction product, an acid content of 0.25% by weight was determined A conversion of 97.5% with a molar ratio of methanol to fatty acids of 20.8:1 was thus achieved. This gives rise to a space-time yield of fatty acid methyl ester of 123.4 g per litre of reactor volume and hour.

Example 1

253 g/h of a mixture of oleic acid and linoleic acid with a content of free fatty acids of 100% by weight was passed with 605 g/h of methanol at a temperature of 83° C. and a pressure of 4 bar once with a residence time of 15 min over a fixed catalyst bed composed of 650 ml of acidic ion exchange resin (corresponds to 121 g of catalyst mass (dry)). The catalyst particles had a diameter of 0.8 mm and were immobilized in a fixed bed reactor with a catalyst bed length of 2.08 m. This gives rise to a catalyst hourly space velocity of 2.1 kg of free fatty acid per kg of catalyst and hour, and a superficial velocity of 2.3 mm/s. In the reaction product, an acid content of 2.8% by weight was determined, i.e. a fatty acid conversion of 97.2% was achieved. This gives rise to a space-time yield of fatty-acid methyl ester of 397.1 g per litre of reactor volume and hour.

Example 2

253 g/h of a mixture of fatty acid methyl ester (97.2% by weight), oleic acid and linoleic acid with a content of free fatty acids of 2.8% by weight was passed with 605 g/h of methanol at a temperature of 83° C. and a pressure of 4 bar once with a residence time of 15 min over a fixed catalyst bed composed of 650 ml of acidic ion exchange resin (corresponds to 121 g of catalyst mass (dry)). In the reaction product, an acid content of 0.24% by weight was determined The catalyst particles had a diameter of 0.8 mm and were immobilized in a fixed bed reactor with a catalyst bed length of 2.08 m. This gives rise to a catalyst hourly space velocity of 0.06 kg of free fatty acid per kg of catalyst and hour, and a superficial velocity of 2.3 mm/s. The starting mixture of this example corresponds to the reaction product of the first esterification stage after removal of water, as described, for example, in example 1. Based on the feedstock of the first esterification stage, a fatty acid conversion of 99.76% was thus achieved.

The invention claimed is:

1. Continuous process for esterifying free fatty acids present in starting materials, comprising the steps of:
   1) removing the free fatty acids from the remaining starting material by distillation or rectification,
   2) reacting the deacidified starting material remaining after step 1) in a transesterification to obtain fatty acid alkyl esters,
   3) reacting the free fatty acids with alcohols using at least one acidic catalyst in a fixed bed, in an esterification reaction,
   4) removing the water formed as a by-product in step 3), optionally together with at least a portion of the alcohol unconverted in step 3),
   5) converting the dewatered product obtained from step 4), with addition of further alcohol, using at least one acidic catalyst in a fixed bed, in an esterification reaction,
   6) mixing the reaction product obtained from step 3) and/or the reaction product obtained from step 5) with the remaining starting material obtained from step 1) and/or the fatty acid alkyl esters obtained from step 2).

2. Process according to claim 1, wherein the at least one acidic catalyst comprises a strongly acidic ion exchange resin.

3. Process according to claim 1, wherein the at least one acidic catalyst comprises a polymeric, macroporous resin with free sulphonic acid groups.

4. Process according to claim 1, wherein step 5) is performed more than once, and the sequence of step 4) and step 5) is optionally performed more than once.

5. Process according to claim 1, wherein the alcohol is added in step 3) in a molar ratio between 5 and 40.

6. Process according to claim 1, wherein reaction (step 3) and/or further conversion (step 5) are carried out at temperatures between 70 and 120° C.

7. Process according to claim 1, wherein a catalyst hourly space velocity of 0.5 to 10 kg of free fatty acid per kg of catalyst an hour exists in step 3) and/or step 5).

8. Process according to claim 1, wherein the pressure in step 3) and/or step 5) is selected to correspond to at least the vapor pressure of the alcohol used.

9. Process according to claim 1, wherein further alcohol is added in step 5).

10. Process according to claim 1, wherein the removal in step 4) is effected by membrane processes or evaporation.

11. Process according to claim 1, wherein a superficial velocity of a fluid phase of the free fatty acids with alcohols in the fixed catalyst bed is 1 to 5 mm/s and the fixed catalyst bed has a length of 1 to 10 m, so as to result in a residence time of less than 30 minutes.

12. A process for producing biodiesel which includes the process of claim 1.

13. Process of claim 5 wherein said molar ratio is between 10 and 25.

14. Process of claim 13, wherein said molar ratio is between 10 and 20.

15. Process of claim 6 wherein said temperatures are between 80 and 95° C.

16. Process of claim 7 wherein said hourly space velocity is between $$1 \text{ and } 5 \frac{\text{kg}}{\text{kg} \cdot h}.$$

17. Process of claim 16 wherein said hourly space velocity is between $$1.5 \text{ and } 4 \frac{\text{kg}}{\text{kg} \cdot h}.$$

* * * * *